United States Patent [19]
Leach et al.

[11] Patent Number: 5,351,008
[45] Date of Patent: Sep. 27, 1994

[54] PORTABLE AND DISPOSABLE DEVICE FOR DETECTING HOLES OR LEAKS IN A SURGICAL OR EXAMINATION GLOVE

[75] Inventors: Eddie D. Leach; Marjorie E. Leach, both of Jonesborough, Tenn.

[73] Assignee: Associated Enterprises, Inc., Jonesboroughs, Tenn.

[21] Appl. No.: 8,219

[22] Filed: Jan. 25, 1993

[51] Int. Cl.$^5$ .................. G01R 31/12; G01M 3/04; A41D 13/12

[52] U.S. Cl. .................. 324/557; 324/556; 340/605; 73/40; 2/11.4; 2/161.7

[58] Field of Search ............... 324/555, 556, 557, 693, 324/694; 320/605; 73/40, 45.4; 2/114, 161.7

[56] References Cited

U.S. PATENT DOCUMENTS

| | | | |
|---|---|---|---|
| 2,981,886 | 4/1961 | Beck | 324/557 |
| 3,252,155 | 5/1966 | Surtees et al. | 340/242 |
| 3,414,808 | 12/1968 | Thomas | 324/557 |
| 3,721,970 | 3/1973 | Niemoth | 340/242 |
| 4,029,889 | 6/1977 | Mizuochi | 174/11 R |
| 4,112,417 | 9/1978 | Himeno | 340/605 |
| 4,558,273 | 12/1985 | Nishimura | 324/54 |
| 4,580,188 | 4/1986 | Brown et al. | 361/212 |
| 4,771,246 | 9/1988 | Boryta et al. | 324/559 |
| 4,776,209 | 10/1988 | Patchel | 73/45.5 |
| 4,799,384 | 1/1989 | Casali | 73/45.5 |
| 4,810,971 | 3/1989 | Marable | 324/557 |
| 4,909,069 | 3/1990 | Albin et al. | 73/40 |
| 4,909,069 | 3/1990 | Albin et al. | 324/557 X |
| 5,036,309 | 7/1991 | Dennison | 340/540 |
| 5,059,913 | 10/1991 | Nigro et al. | 324/557 X |
| 5,196,799 | 3/1993 | Beard et al. | 324/557 |
| 5,204,632 | 4/1993 | Leach | 324/557 |

FOREIGN PATENT DOCUMENTS

| | | |
|---|---|---|
| 919775 | 1/1973 | Canada . |
| 942873 | 2/1974 | Canada . |
| 983579 | 2/1976 | Canada . |
| 1028392 | 3/1978 | Canada . |
| 1094157 | 1/1981 | Canada . |
| 1191202 | 7/1985 | Canada . |
| 1199969 | 1/1986 | Canada . |
| 859579 | 1/1961 | United Kingdom . |

OTHER PUBLICATIONS

Proofs, Apr. 1989, p. 17, Penwell Publishing Company, 1421 S. Sheridan, Tulsa, Okla. 74112.
Judy Jakush, "Governemnt Getting Ready to Test Gloves", ADA News, Apr. 3, 1989, pp. 22–23.
Holstein, Howard M., "Designing Quality In", Medical Device & Diagnostic Industry, pp. 32, 34–35.
Cobetti, John P.; Cerminaro, Michael and Shipman, Charles Jr., "Hand Asepsis: The Efficacy of Different Soaps in the Removal of Bacteria from Sterile, Gloved Hands", JADA, vol. 113, Aug. 1986, pp. 291–292.
Klein, Robert C.; Party, Esmeralda and Gershey, Edward L., "Virus Penetration of Examination Gloves", BioTechniques, vol. 9, No. 2, (1990) pp. 196–199.
Leters to the Editor, ADA, Oct. 1, 1990, 1 page.
Letters to the Editor, JADA, vol. 114, Jan. 1987, pp. 14 & 16.
Walter, Carl W., and Kundsin, Ruth B., "The Bacteriologic Study of Surgical Gloves from 250 Operations", Surg. Cynecol. Abstract 128: 1969, pp. 949–952.
"Electronics device for the detection of breaches in asepsis during surgical procedures", Br. J. Surg. 1987, vol. 74, Nov. 1038–1039.
Russell, Thomas R., M.D.; Rogue, Francis E., M.D.; and Miller, Fletcher A., M.D., A New Method for Detection of the Leaky Glove, A Study on Incidence of Defective Gloves and Bacterial Growth From Surgeons' Hands; Arch Surg. vol. 93, Aug. 1966.

*Primary Examiner*—Gerard R. Strecker
*Assistant Examiner*—Diep Do
*Attorney, Agent, or Firm*—Luedeka, Neely & Graham

[57] ABSTRACT

Portable and disposable apparatus for leak testing surgical and/or examination gloves which may be worn on the body of the user to permit convenient detection of glove leaks during diagnostic procedures. In one embodiment there is provided an electrolyte-containing pouch worn on the body of the user and into which gloved hands may be inserted for evaluation. A leak in a glove permits the electrolyte to penetrate the glove and contact the skin of the wearer to close an electrical circuit and trigger an alarm.

7 Claims, 3 Drawing Sheets

PORTABLE AND DISPOSABLE DEVICE FOR DETECTING HOLES OR LEAKS IN A SURGICAL OR EXAMINATION GLOVE

The present invention relates generally to devices for detecting leaks or faults in materials. More particularly, the present invention relates to a portable, disposable apparatus worn by health care personnel for testing of surgical and examination glove integrity.

Acquired Immune Deficiency Syndrome ("AIDS") and hepatitis are two of the many communicable infectious diseases which bring death and discomfort to many. Communicable diseases are often spread by exposure of noninfected persons to the blood or other body fluids of infected individuals. Health care personnel performing surgical or diagnostic procedures on infected patients are at high risk of exposure to infected blood and other body fluids and vice versa. To protect against exposure to disease, health care personnel typically wear latex gloves to provide a barrier between the wearer's hands and the body fluids.

In the manufacture of surgical and examination gloves, there is a risk that a glove may contain a pinhole or other path through which fluids, particularly contaminated body fluids, could pass. In addition, it is not uncommon for gloves to develop leaks during use. For example, medical or dental instruments and sharp bone or tooth fragments, etc., can easily puncture gloves and thereby expose both the wearer and the patient to the body fluids of the other. In addition, gloves may also puncture from the interior, such as by a hangnail on the wearer's finger.

A variety of devices are known in the art for testing the integrity of these gloves. However, such devices typically require electrical contact between the user and other equipment such as remotely located basins of water or saline solution or the patient. In addition, the use of basins of water or saline solution may result in cross-contamination.

It is therefore an object of the present invention to provide an improved device for leak testing surgical and/or examination gloves.

It is a further object of the present invention to provide a testing device of the character described which is portable.

Still another object of the present invention is to provide a testing device of the character described which prevents cross-contamination.

It is a still further object of the present invention to provide a testing device of the character described which is self-contained on the body of the user.

It is yet a further object of the present invention to provide testing device of the character described which does not require electrical contact between remotely located containers of water or saline solution or the patient.

It is a still further object of the present invention to provide a testing device of the character described which is easy to use and economical.

As will be seen, the present invention provides a glove test unit which is disposable and portable, and which is contained completely on the person of the health care worker. No other person or remote container of test solution is needed, nor are any peripheral electrical connections to a remote unit or to a patient required. This gives the health care worker freedom from restraints caused by electrical leads connecting to the patient or to remote units and therefore allows unlimited movement and freedom for the worker. In addition, because that portion of the unit which is subject to contamination is disposable, the unit may be personal to a particular health care worker for a particular patient. The contaminated portion is thereafter disposed of to reduce cross-contamination and thereby avoid the spread of disease.

Stated generally, the present invention provides an apparatus for detecting holes or leaks in gloves, particularly surgical and examination gloves, worn on the hand of a user. The apparatus comprises a first electrically conductive lead having a first end connected to an electrical power test unit ant a second end in electrical continuity with the body of the user; a second electrically conductive lead having a first end connected to the electrical power test unit and a second end in electrical continuity with an absorbent material positioned within a fluid impervious covering worn on the body of the user, the absorbent material being capable of absorbing and containing an electrolyte solution; an opening extending through the fluid impervious covering and in communication with a cavity defined in the absorbent material for insertion of the gloved hand therein for contacting the electrolyte solution to test for leaks in the glove; and means for measuring electrical properties between the first and second leads when the electrolyte solution passes through at least one of the holes in the inserted glove and causes a completion of an electrical circuit between the first lead and the second lead, the means for measuring being in electrical continuity with the first lead and the second lead.

Other objects, features and advantages of the present invention will become apparent upon reading the following detailed description of an embodiment of the invention, when taken in conjunction with the accompanying drawings in which.

The present invention is described in detail for its primary use in detecting leaks, tears and/or pinholes in surgical and/or examination gloves. It is to be understood, however, that the apparatus of the invention may easily be adapted for use with many other articles having similar properties and uses.

Most surgical or examination gloves are made of some type of latex rubber or plastic or synthetic material which acts as a dielectric. That is, it will not allow the passage of ions which are driven by a given voltage unless there is a path in the form of a tear or other perforation in the membrane forming the glove.

Ions are considerably smaller than the smallest of the known infectious agents, viruses. Bacteria are considerably larger than viruses. Therefore, if a glove is impervious to ions driven by an electric potential, then the glove should also be impervious to viruses and other infectious agents, which are many times larger than the ions, and are not driven by any electric potential. If ions can pass through a glove, then the glove should be judged defective and should be discarded, thus protecting both the patient and the health care professional.

Figure 1:
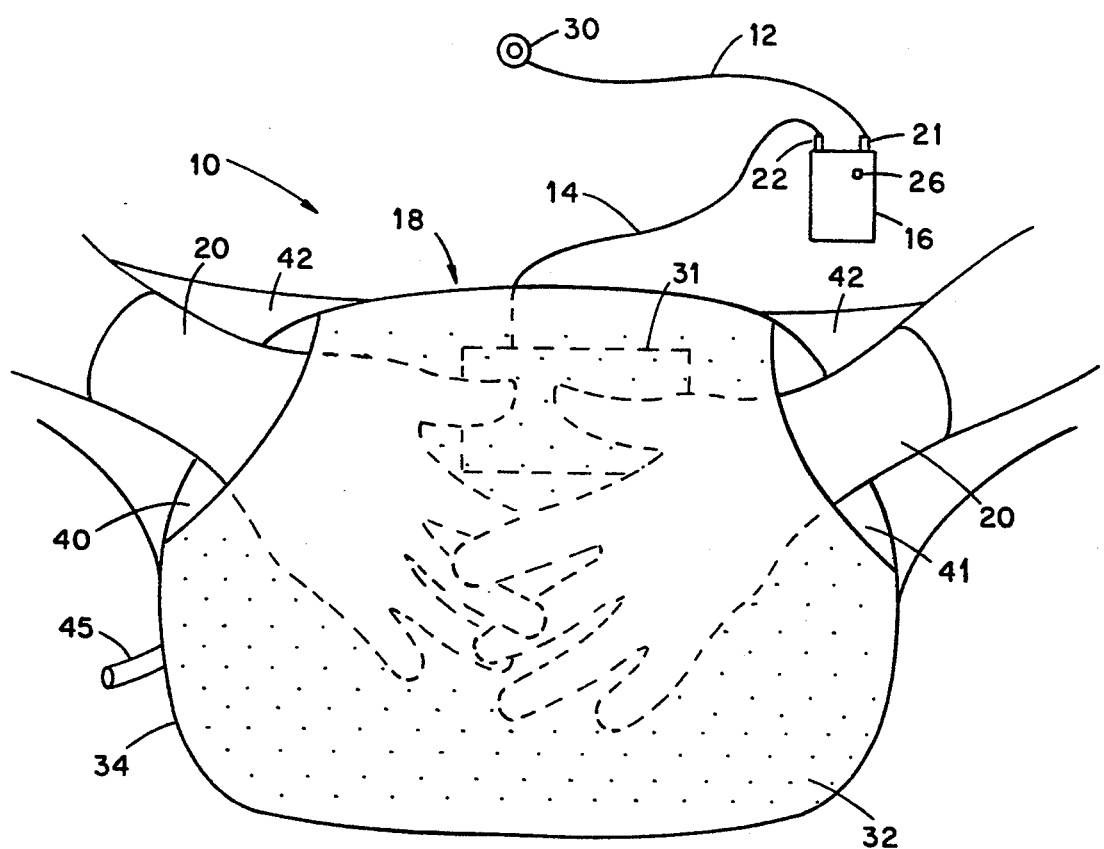
FIG. 1 is a cross-sectional frontal view of a testing device provided in accordance with the present invention.
Figure 2:
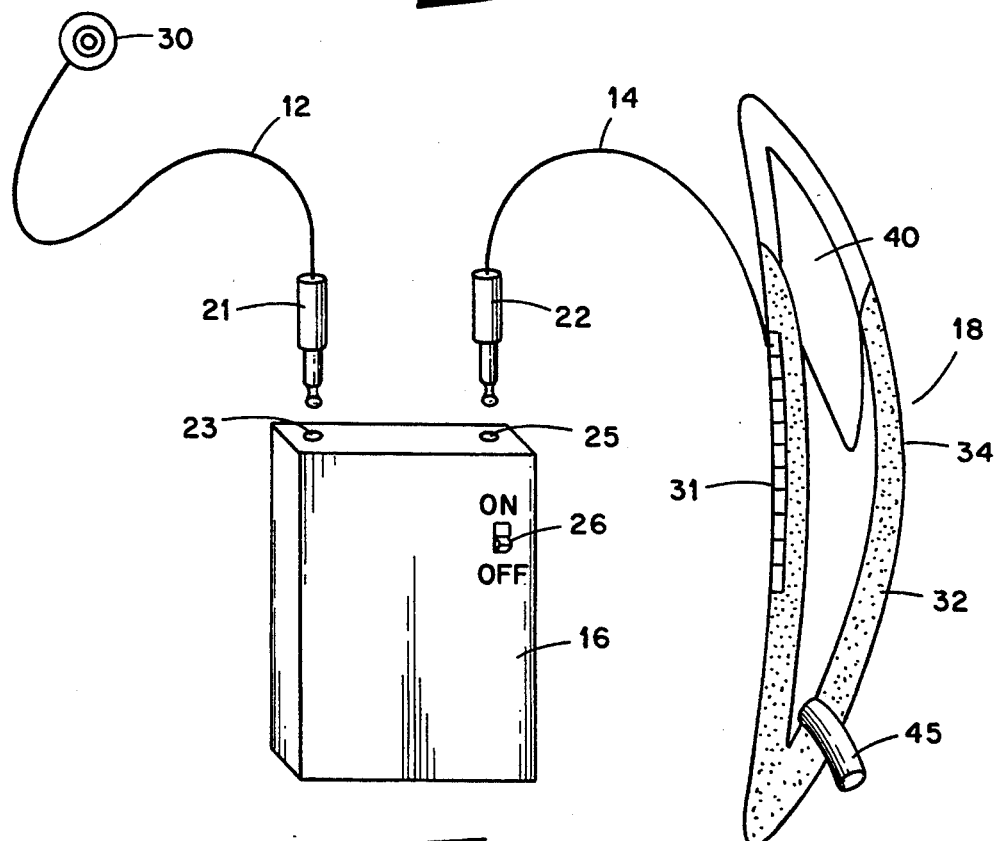
FIG. 2 is a cross-sectional side view of the apparatus of FIG. 1.

Referring now to FIGS. 1 and 2, in a preferred embodiment, testing apparatus 10 of the present invention includes a first test lead 12, a second test lead 14, an electrical powered test unit 16, and a test pouch 18. A health care worker inserts each gloved hand 20 into the test pouch 18 to test the integrity of the gloves, as will be described in more detail below. The apparatus is completely and conveniently contained on the person of the health care worker and is not in electrical contact with the patient or remote from the worker. Thus, the present invention does not provide pathways for current to flow from the health care worker to the patient other than through a glove.

The test leads 12 and 14 are conventional test leads for use with low voltage current applications, and are preferably about 24 inches in length each and formed of insulated wire of between about 22 to 26 gauge. The leads 12 and 14 include connectors 21,22, respectively, to allow the leads 12 and 14 to each be connected to one pole of the test unit 16.

The test unit 16 is a low voltage (AC or DC) electrically powered test unit and may be powered by a battery for portability. The present embodiment is described in conjunction with a DC test unit. The test unit includes an alarm, such as a buzzer, which indicates when the circuit provided by the invention is closed, such as when a glove has a leak. A preferred circuit diagram for the test unit is shown in detail in FIG. 5, and will be described more fully below.

In the illustrated embodiment, the lead 12 is connected to one pole 23, and the lead 14 is connected to the other pole 25. It has been experienced that the particular polarity of the leads does not affect the test procedure. The test unit 16 is controlled by an on/off switch 26.

The other end of the lead 12 connects to an electrode 30, preferably of a type commonly utilized in EKG diagnostic procedures. The electrode 30 is positioned on the body of the user during testing, as will be explained below. The other end of the lead 14 connects to a conductive membrane 31 in electrical contact with test pouch 18.

Figure 3:
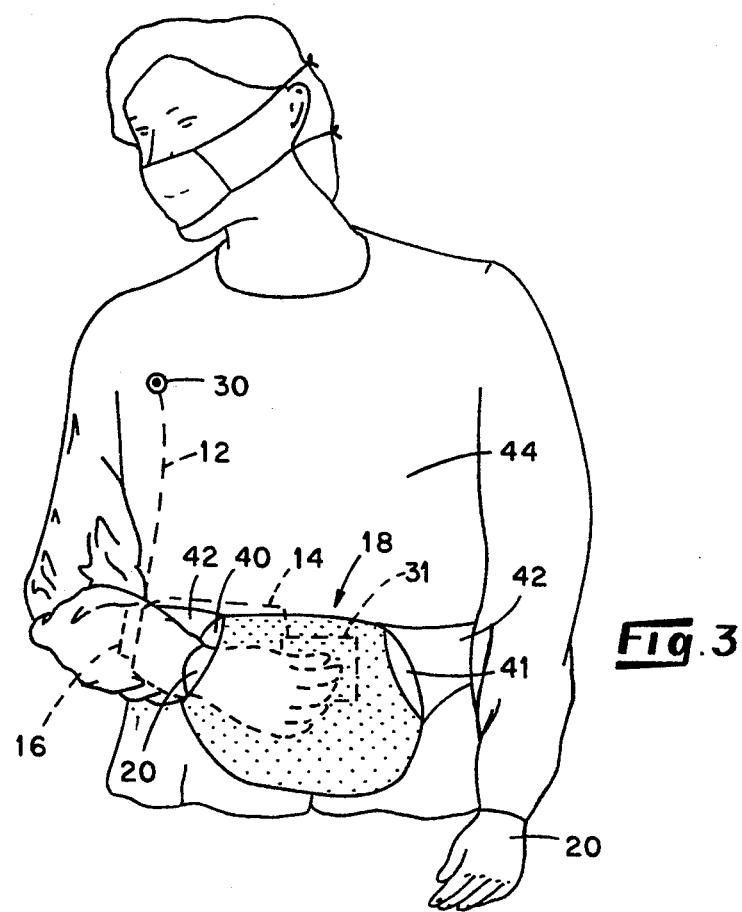
FIG. 3 is pictorial view of a preferred embodiment, showing a health care worker wearing testing apparatus in accordance with the present invention.
Figure 4:
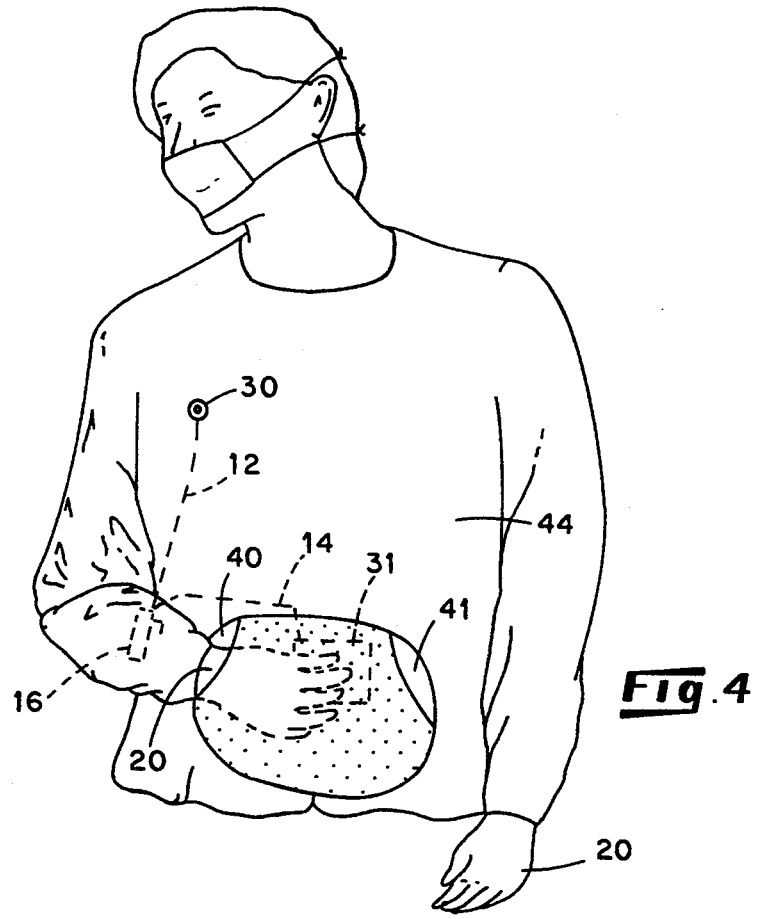
FIG. 4 is a pictorial view of an alternate embodiment of the present invention wherein testing apparatus is formed as part of a disposable surgical gown or other uniform.

With additional reference to FIG. 3, the pouch 18 is a sack-like structure which is constructed so that it has a waterproof material 32 on the outside and an absorbent material 34, such as a sponge or gauze pad, on the inside. Openings 40 and 41 are provided at opposite ends of the pouch 18 and provide passages for insertion of the gloved hands therein. The depicted openings are slits that remain substantially closed when gloved hands are not inserted therein. This serves to isolate the interior of the pouch from the operator so that airborne contaminants are prevented from entering the pouch. The pouch 18 is light weight so as to be portable and may be secured to the wearer by straps 42 or, alternatively, may be integrally formed as part of a surgical gown or uniform 44, shown in FIG. 4. The portability of the pouch is advantageous in that the pouch may be carried by the health care worker at all times such that the worker is not required to interrupt the diagnostic procedure to travel to a test unit to check for a glove leak.

The material which forms the outside of the pouch may be of a plastic which will provide waterproof insulation between the health care worker and the absorbent material. Preferably, the material 32 is a waterproof plastic sheet and a layer of the absorbent material 34 is bonded to one side thereof. This laminate is folded back upon itself with the overlying opposite top and bottom edges being bonded to one another while leaving the side edge unbonded to provide the openings 40,41. In addition, the electrically conductive membrane 31 may be inserted within the pouch to connect the lead from the test unit to the absorbent material 34 containing the electrolyte solution. An electrolyte solution, such as tap water or a saline solution commonly available in health care settings is introduced to the absorbent material for absorption thereby. To this end, a tube 45 may be provided between the interior and exterior of the pouch 18 for introducing or withdrawing the electrolyte solution. A valve (not shown) may be provided on the exterior end of the tube 45 to prevent leakage. Alternatively, the solution may be contained in a capsule or other container within the pouch 18 and released to moisten the absorbent material. In addition, a surface wetting agent and/or an antimicrobial material may be added to the electrolyte solution.

The absorbent material 34 should have sufficient capillary action to become evenly wetted by the electrolyte solution at a ratio of approximately 0.05 to 0.10 ml/cm$^2$ of pouch inner surface area. The salinity or ionic strength of the electrolyte solution used to moisten the absorbent material in the pouch should be sufficient to be electrically conductive. The amount of the solution used should be sufficient to assure proper wetting of the interior of the pouch, but not so much as to spill out of the openings.

Figure 5:
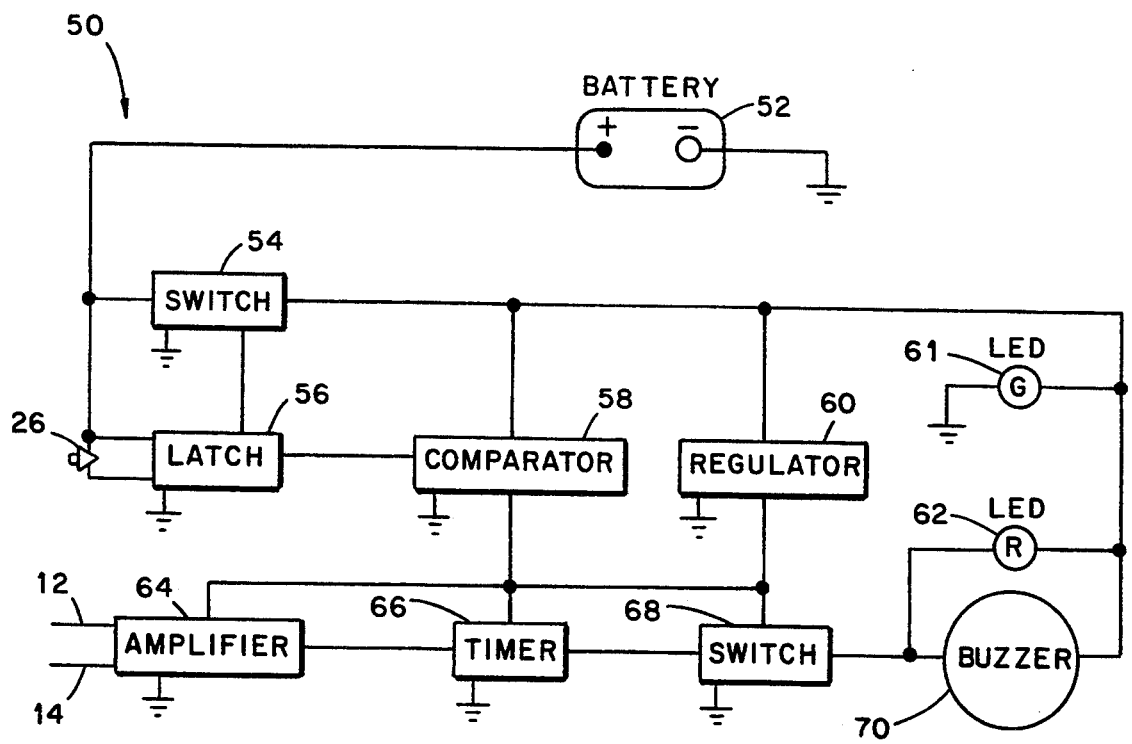
FIG. 5 is a circuit diagram of the testing apparatus of the present invention.

With reference now to FIG. 5, there is shown a diagram of a circuit 50 of the test unit 16. The circuit 50 is powered by a nine volt battery 52 activated by the on/off switch 26 and includes switch 54, latch 56, comparator 58, regulator 60, green light emitting diode (LED) 60, red LED 62, amplifier 64, timer 66, switch 68, and buzzer 70.

Turning the on/off switch 26 to the "on" position activates the battery 52 to supply voltage to the latch 56 which latches and applies voltage to the switch 54 to keep the switch 54 held on so that the battery voltage is applied to the comparator 58, the regulator 60, the LEDs 60,62 and the buzzer 70. The green LED 60 remains illuminated to indicate that the unit is on.

The regulator 60 then applies regulated voltage of 3 volts to the comparator 58, the amplifier 64, the timer 66 and the switch 68. The comparator 58 compares the 3 volts from the regulator 60 with the battery voltage from switch 54 and when the battery voltage drops 20 percent the comparator 58 triggers the latch 56 so that the switch 54 is turned off and the unit will not operate when the battery voltage is below 7.2 volts.

The amplifier 64, timer 66 and switch 68 operate at a regulated volts regardless of the battery voltage. The test leads 12,14 connect to the amplifier and have less than 1.5 volts across them. This voltage across the leads 12,14 drops to less than 0.15 volts when the leads activate the amplifier 64, as when a leak in the gloves occurs, and the leads draw a maximum current of 0.27 microamps or less.

When a leak in the gloves occurs, the amplifier 64 turns on the timer 66, which in turn activates the switch 68 for ½ second. The switch 68 then grounds the buzzer 70 and the red LED 62 so that the buzzer sounds and the red LED illuminates to indicate a defective glove. If the defect is no longer detected at the end of ½ seconds, the timer 66 resets and the buzzer and red LED turn off.

In actual use, the health care worker places his or her gloved hands into the waterproof pocket of the pouch to contact the absorbent material moistened with saline or other electrically conductive solution. This action may be done to clean the gloves in the saline solution or whenever desired by the health care worker, such as at the beginning of the procedure, at convenient times during the procedure, or at the end of the procedure. By massaging the wet gloved hand(s) in the pocket while contacting the moistened absorbent material, the wearer may force normally closed holes in the glove material open to allow electrolyte to penetrate the opening(s) and contact the skin of the wearer. It has been experienced that the opening through the thickness of the glove need not directly contact the moistened absorbent material, it being observed that current may flow over the wet surface of the glove and make an electrical connection between the absorbent material and the perforation or leak in the glove. To this end, it will be noted that the use of a surface active agent or wetting agent in the electrolyte solution facilitates wetting of the gloved surface. A leak (perforation) in a glove permits electric current to flow through the glove material to close the previously open circuit 50 between the leads.

The closed electrical circuit supplies an electrical current to the red LED and the buzzer to illuminate the red LED and trigger a beep response by the test unit to inform the wearer that a leak has occurred. In this respect, it will be appreciated that the buzzer may be connected by a lead to an earphone worn in the wearer's ear. This will prevent the buzzer from distracting others who may not be aware that the gloves are being tested.

In addition, the buzzer may be silenced by withdrawing the glove from the pouch. This is advantageous to minimize the distracting effect of the buzzer. The hand with the leakage of current may be identified by placing first one hand, then the other, in the pocket. The glove with the leakage of current produces a beep when placed in the pocket and contacted with the electrolyte moistened absorbent material. At any time desired during the operative procedure, the health care worker may check either or both glove(s) for current leaks by placing the gloved hand(s) in the pocket.

Another advantage of the present invention is that the health care worker is not required to be attached electrically, such as by a wire lead, to the patient. Thus, it will be appreciated that any electric current flowing from the health care worker to the patient must pass through the glove(s). This reduces the possibility of electrical shock when the use of electrical instruments is required, and is especially advantageous when the diagnostic procedure is performed in a facility having a conductive floor, such as is often provided in operating rooms to prevent build up of static electricity in the presence of flammable gases.

The apparatus of the present invention may be constructed of relatively inexpensive materials so as to be considered disposable. This is advantageous in that it permits the contaminated portion of the apparatus to be disposed of after each diagnostic procedure. This eliminates the need to sanitize the apparatus between uses and reduces the risk of spreading disease from patient to patient.

Accordingly still another advantage of the present invention is provided by the disposal of the contaminated portion. The Occupational Safety and Health Administration ("OSHA") requires that disposable (single use) surgical gloves shall be replaced as soon as practical when contaminated and that disposable gloves shall not be washed or decontaminated for reuse, [Federal Register Vol. 56, No. 235, p 64177 (ix) (A)-(B) (Dec. 6, 1991). The testing of gloves with prior art devices having a basin which is used for more than one patient could possibly result in contamination of the gloves. Conversely, the testing of gloves with the present invention, wherein the pouch is single use eliminates this possible source of contamination.

A still further advantage results from the structure of the pouch wherein the pouch openings are substantially isolate the interior of the pouch from the environment of the operator to prevent airborne contaminants from entering the pouch. For example, in many health care procedures where certain pieces of equipment are used, such as bone cutters, high speed dental handpieces, ultrasonic dental scalers, and the like, minute aerosol droplets are created which are dispersed into the air of the operator. These droplets contain microbes from the patient as well as those additional microbes which may be picked up as these droplets float through the air. These droplets readily settle into open basins of test liquid. Isolation of these droplets from the interior of the pouch eliminates this occurrence.

While this invention has been described in detail with particular reference to preferred embodiments thereof, it will be understood that variations and modifications may be made without departing from the spirit and the scope of the invention as described hereinbefore and as defined in the following claims.

What is claimed is:

1. An apparatus for detecting holes or leaks in a surgical or examination glove worn on the hand of a user, said apparatus comprising:
   a first electrically conductive lead having a first end connected to an electrical power test unit and a second end in electrical contact with the body of the user;
   a second electrically conductive lead having a first end connected to said power test unit and a second end in electrical contact with an absorbent material positioned within a fluid impervious covering worn on the body of the user, said absorbent material being capable of absorbing and containing an electrolyte solution;
   an opening extending through said covering and in communication with a cavity defined in said absorbent material for insertion of the gloved hand therein for contacting said electrolyte solution to test for leaks in the glove; and
   means for measuring electrical properties between said first lead and said second lead when the electrolyte solution enters said glove through a leak in said glove and causes a completion of an electrical circuit between said first lead and said second lead, said means for measuring being in electrical continuity with said first lead and said second lead and producing an output signal in response to the completed electrical circuit indicative of a leak in the glove.

2. The apparatus of claim 1, wherein the second end of the first electrically conductive lead comprises an EKG electrode.

3. The apparatus of claim 1, wherein the absorbent material comprises a sponge, and the fluid impervious covering comprises plastic.

4. The apparatus of claim 1, wherein the electrolyte solution comprises a saline solution.

5. The apparatus of claim 1, wherein the means for measuring electrical properties comprises an alarm which sounds when the electrical circuit is completed.

6. The apparatus of claim 1, further comprising strap means for securing the apparatus to the body of the user.

7. A surgical gown, comprising:

a body portion;

arm portions connected to the body portion; and an apparatus attached to the body portion of the gown for detecting holes or leaks in a surgical or examination glove worn on the hand of a user, the apparatus comprising:

a first electrically conductive lead having a first end connected to an electrical power test unit and a second end in electrical contact with the body of the user, a second electrically conductive lead having a first end connected to the power test unit and a second end in electrical contact with an absorbent material positioned within a fluid impervious covering worn on the body of the user, the absorbent material being capable of absorbing and containing an electrolyte solution, an opening extending through the covering and in communication with a cavity defined in the absorbent material for insertion of the gloved hand therein for contacting the electrolyte solution to test for leaks in the glove, and means for measuring electrical properties between the first lead and the second lead when the electrolyte solution enters the glove through a leak in the glove and causes a completion of an electrical circuit between the first lead and said second lead, the means for measuring being in electrical continuity with the first lead and the second lead and producing an output signal in response to the completed electrical circuit indicative of a leak in the glove.

* * * * *